(12) United States Patent
Thomas et al.

(10) Patent No.: US 12,193,724 B2
(45) Date of Patent: Jan. 14, 2025

(54) DRIVE SHAFT FOR A SURGICAL INSTRUMENT

(71) Applicant: GYRUS MEDICAL LIMITED, Cardiff (GB)

(72) Inventors: Daniel John Thomas, Cardiff (GB); Bryan Tissington, Cardiff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 628 days.

(21) Appl. No.: 17/156,129

(22) Filed: Jan. 22, 2021

(65) Prior Publication Data

US 2021/0298820 A1    Sep. 30, 2021

(30) Foreign Application Priority Data

Mar. 31, 2020    (GB) ..................................... 2004697

(51) Int. Cl.
*A61B 18/14*    (2006.01)
*A61B 18/00*    (2006.01)
*A61B 18/12*    (2006.01)

(52) U.S. Cl.
CPC .. *A61B 18/1442* (2013.01); *A61B 2018/0063* (2013.01); *A61B 2018/126* (2013.01); *A61B 18/1445* (2013.01); *A61B 2018/1455* (2013.01)

(58) Field of Classification Search
CPC ............ A61B 18/1442; A61B 18/1445; A61B 2018/0063; A61B 2018/126; A61B 2018/1455
See application file for complete search history.

(56) References Cited

U.S. PATENT DOCUMENTS

2013/0296848 A1* 11/2013 Allen, IV ............... A61B 17/29
606/41
2014/0025071 A1    1/2014 Sims et al.
(Continued)

FOREIGN PATENT DOCUMENTS

JP      2017-035615 A    2/2017
WO      2018/200240 A1   11/2018

OTHER PUBLICATIONS

May 17, 2022 Office Action issued in Japanese Patent Application No. 2021-034926.
(Continued)

*Primary Examiner* — Khadijeh A Vahdat
(74) *Attorney, Agent, or Firm* — Ee Ming T. Bahk (57) ABSTRACT

The present invention provides a drive shaft for a bipolar surgical instrument, the drive shaft comprising an elongate body defining a first axis, and having a proximal end portion and a distal end portion, the elongate body comprising: a first portion defining a first open channel extending along a portion of the length of the elongate body; and a second portion distinct from the first portion, the second portion defining a second open channel extending along a portion of the length of the elongate body, wherein both the first and second portions are aligned with one another and extend parallel to the first axis, and wherein the first portion is spaced apart from the second portion so as to define a recessed blade track therebetween, the recessed blade track extending parallel to the first axis. The present invention further provides a bipolar surgical instrument incorporating such a drive shaft.

9 Claims, 6 Drawing Sheets

(56) References Cited

U.S. PATENT DOCUMENTS

2017/0196624 A1    7/2017  Nagtegaal et al.
2020/0297404 A1    9/2020  Cosmescu

OTHER PUBLICATIONS

Sep. 3, 2020 Search Report issued in Great Britain Patent Application No. GB2004697.5.
Aug. 27, 2024 Search Report issued in British Patent Application No. GB2412217.8.

* cited by examiner

DRIVE SHAFT FOR A SURGICAL INSTRUMENT

The present invention relates to a drive shaft for operating the jaws of a surgical instrument, and specifically to a drive shaft defining a blade track. The present invention also relates to surgical instruments having such a drive shaft.

BACKGROUND OF THE INVENTION

Bipolar surgical instruments are used to clamp and seal tissue, particularly blood vessels, during surgical procedures. Clamping is typically achieved using a pair of opposed jaws that are remotely operable to clamp around the tissue being sealed. Sealing is typically achieved using application of radio frequency energy delivered to the tissue being sealed by electrodes mounted on the opposed jaws of the instrument.

Bipolar surgical instruments may also include cutting blades that enable a surgeon to cut tissue using the same instrument as used for clamping and sealing of that tissue. In such instruments, it is important that the cutting blade is suitably supported though the shaft of the instrument and easily moved between a retracted position and a deployed position in which it extends further along the jaws of the instrument to cut the tissue. Failure to suitably support and guide the cutting blade through the shaft of the instrument can result in misalignment of the cutting blade relative to the jaws. Such misalignment is common when the instrument is in use and grasping tissue.

Accordingly, it is desirable to provide an instrument that addresses such issues.

SUMMARY OF THE INVENTION

Aspects of the present invention are set out in the attached claims.

According to one exemplary aspect, there is provided a drive shaft for a bipolar surgical instrument, the drive shaft comprising: an elongate body defining a first axis, and having a proximal end portion and a distal end portion, the elongate body comprising: a first portion defining a first open channel extending along a portion of the length of the elongate body; and a second portion distinct from the first portion, the second portion defining a second open channel extending along a portion of the length of the elongate body, wherein both the first and second portions are aligned with one another and extend parallel to the first axis, and wherein the first portion is spaced apart from the second portion so as to define a recessed blade track therebetween, the recessed blade track extending parallel to the first axis.

The second portion is distinct from the first portion i.e. the two portions are non-integral. By using separate portions, rather than one single portion bend to form two parallel portions, the problems encountered during manufacture in making an accurate U-shaped bend in a planar member are avoided.

Alternatively, the first and second open channels comprise tube-like channels. Wires and cables etc are supported along the elongate body within the channels. After insertion into the channel from either the proximal or distal end of the elongate body, the wires and/or cables can be fed through the tube-like channels until they extend out of the opening at the other end of the channel. There is no opportunity for the wires and/or cables to leave the tube-like channels except via the openings at each end of each respective tube-like channel.

In one embodiment, the drive shaft is further provided with a spacer portion located between the first and second portions. The width of the spacer portion determines how far apart the first and second portions are held relative to one another. Further, the height of the space portion and it's position between the first and second portions determines how wide the resultant blade track will be.

It is preferred that the blade track is of uniform dimensions along at least a portion of it's length i.e. where it is within a surgical instrument housing and linked to a blade deployment mechanism. Therefore, it is preferable that the spacer is of equal width along it's length to ensure that the blade track remains parallel.

Preferably, the first and second portions are welded to the spacer portion. However, other forms of engagement may be used in addition to, or as an alternative to, welding to hold the first and second portions together. For example, the first and second portions may be adhered together or secured together using suitable pins, screws, rivets or other suitable forms of mechanical engagement.

Alternatively, the first and second portions and the spacer portion may be formed integrally with one another. For example, a cut out portion may be provided in one of the first and second portions. Such a cut-out portion may be bent to form an L-shaped member to act as a spacer between the first and second portions. One leg of the L-shaped member of the first or second portion may be secured to the other of the first or second portion to secure the first or second portions together whilst the other leg of the L-shaped member serves to space the first and second portions from one another.

Preferably, the one leg of the L-shaped member of the first or second portion that is secured to the other of the first or second portions is secured by welding. However, other forms of engagement may be used in addition to, or as an alternative to, welding. For example, the first and second portions may be adhered together or secured together, via the L-shaped member, using suitable pins, screws, rivets or other suitable forms of mechanical engagement.

In one embodiment, each of the first and second portions defines a blade engagement surface for engagement with a blade of a surgical instrument. Each respective blade engagement surface is located facing the other to form a blade track therebetween into which a retractable blade may be received, in use.

In one embodiment, the first and second open channels are located adjacent the proximal end portion of the elongate body. Wires and/or cables may be extended through one or both channels during use to guide them along the elongate body and keep them separate from any other internal components of the surgical instrument in which the drive shaft is located, during use.

The elongate body may further comprise a cam slot adjacent the distal end portion configured for engagement with first and second jaws of a surgical instrument. The cam slot is dimensioned to receive a securing pin or other suitable securing means therethrough in use, to allow the drive shaft to operate to move the jaws of the surgical instrument relative to one another during use.

A second aspect of the present invention provides a bipolar surgical instrument comprising a body; an elongate shaft attached to the body, the elongate shaft extending to a distal end; first and second opposed jaws located at the distal end of the elongate shaft, the first jaw being movable with respect to the second jaw between an open position in which the first and second jaws are spaced apart from one another, and a closed position in which the first and second jaws are adjacent one another, the first and second jaws defining respective inner surfaces; a drive shaft according to a first aspect of the present invention, the drive shaft connected with at least the first jaw, the drive shaft being movable with respect to the body and the elongate shaft between a first position in which the jaws are in the open position, and a second position in which the jaws are in the closed position; an actuation grip movably mounted on the body, and arranged to operate the drive shaft, the actuation grip having a released position in which the drive shaft is in the first position, and an engaged position in which the drive shaft blade track is in the second position; and a blade as claimed in any one of the preceding claims, the blade extending through the recessed blade track in the drive shaft to the first and second jaws, and wherein each of the first and second opposed jaws defines a respective blade track which extends from the proximal end towards the distal end of the jaw concerned.

In one embodiment, the bipolar surgical instrument further comprises a blade actuator operable to move the blade between a retracted position and a deployed position, in which the blade moves within the recessed blade track.

In one embodiment, wires for the operation of other functions of the instrument e.g. tissue retrieval bag operation and the like, extend through respective first and second open channels. This ensures that the wires are kept away from, and thus incur no damage from, the blade actuator

BRIEF DESCRIPTION OF THE DRAWINGS

An embodiment of the present invention will now be described by way of example only and with reference to the following drawings in which.

DETAILED DESCRIPTION OF THE PREFERRED EMBODIMENTS

Figures 1A, 1B, 1C:
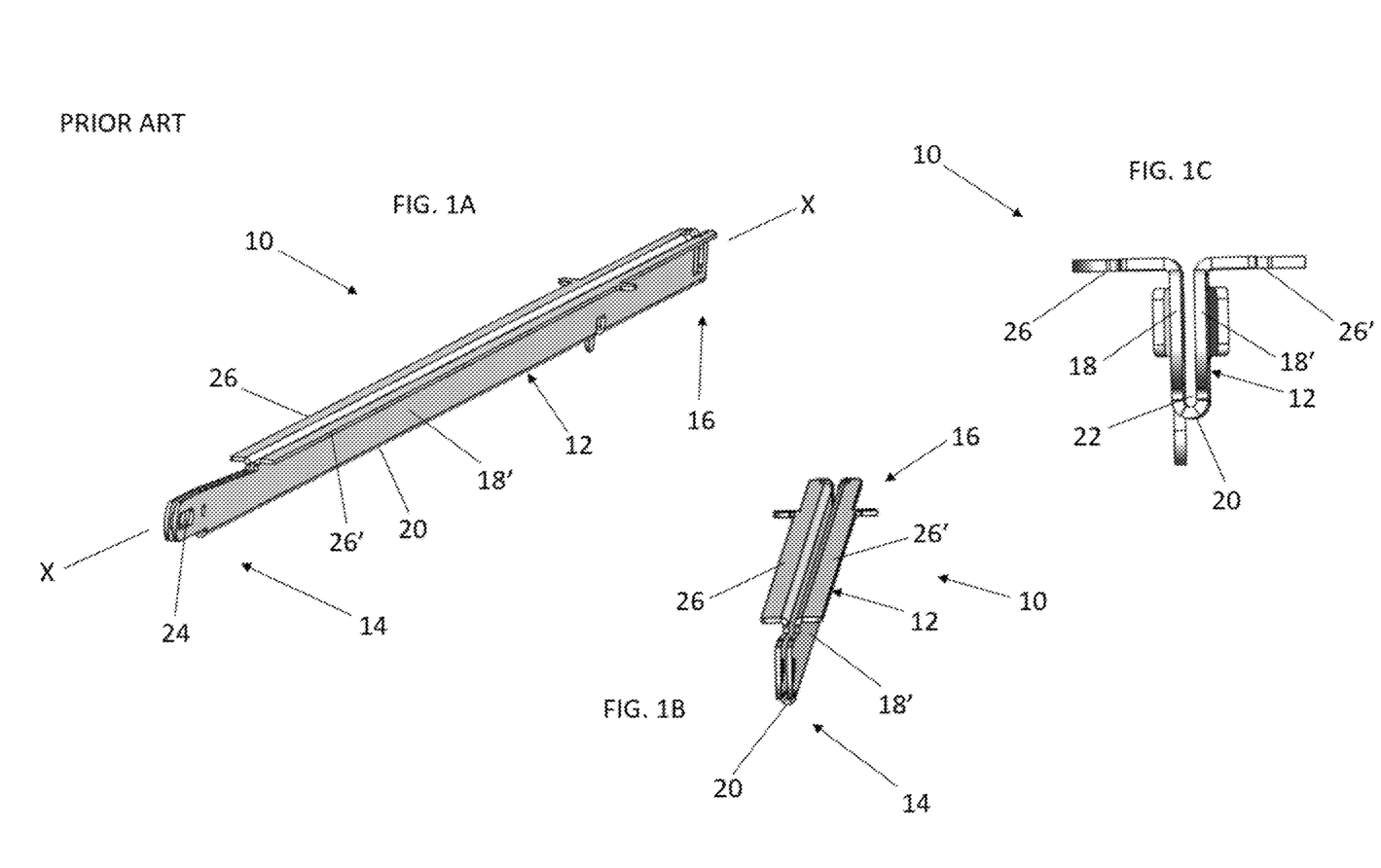
FIG. 1A is a perspective view from below and one side of a prior art drive shaft.
FIG. 1B is a perspective view from the front of the prior art drive shaft of FIG. 1A.
FIG. 1C is a view from one end of the prior art drive shaft of FIG. 1A.

FIGS. 1A to 1C describe a prior art drive shaft 10 for a surgical instrument. Drive shaft 10 comprises an elongate body 12 having a distal end 14 and a proximal end 16, elongate body 12 defining an axis X as shown in FIG. 1A.

Elongate body 12 comprises two substantially planar members 18, 18' extending along a portion of the length of elongate body 12, planar members 18, 18' being parallel to one another along their length. Planar members 18, 18' are connected to one another by means of U-shaped portion 20 so as to form a uniform channel 22 extending along elongate body 12. The U-shaped cross-sectional shape is essential to correctly space planar members 18, 18' from one another, as channel 22 comprises a blade track within which a retractable blade (not shown) extends during use.

Substantially planar members 26, 26' extend substantially perpendicularly from respective planar members 18, 18' distal to U-shaped portion 20. Planar members 18, 18' from proximal end 16 towards distal end 14 of elongate body 12. Planar members 26, 26' serve to provide a surface extending along both side of blade track channel 22 within which a retractable blade (not shown) moves during use. The position of the junction between planar members 18, 18' and respective planar member 26, 26' is critical to define the height of the blade track. This height must be accurate and consistent along the length of the elongate body 12 to ensure smooth movement of a retractable blade (not shown) during use when received within channel 22.

Distal end 14 of elongate body 12 is provided with a cam slot 24 for engagement with first and second jaws of a surgical instrument (not shown). Cam slot 24 is held in place relative to the first and second jaws using a pin (not shown) that extends through and is secured in place within cam slot 22.

Elongate body 12 is of single piece construction and is formed by bending a planar template piece to form the U-shaped portion 20 to create channel 22.

It is critical that, during manufacture, channel 22 is uniform along its length i.e. that the distance between planar members 18, 18' is consistent along the length of channel 22 and that the bend between planar member 18, 18' and planar members 26, 26' is accurate placed to ensure that channel 22 is of uniform depth along its length. This depends on highly accurate manufacture of elongate member 12 and specifically high precision bending during manufacture i.e. both placement of bends and accuracy of angle of bending.

However, to form such bends along elongate body 12 of significant length compared to it's relatively narrow width is very difficult. Any inaccuracies in the forming of channel 22 during manufacture will result in potential misalignment of the blade within the channel 22 and thus interfere with the smooth movement of a retractable blade within channel 22 during deployment and retraction when carrying out surgical procedures.

Therefore, the forming of multiple bends of a single elongate metal piece is insufficiently reliable and accurate for surgical requirements.

FIGS. 2 to 5 show a first embodiment of a drive shaft in accordance with a first aspect of the present invention.

Figure 2:
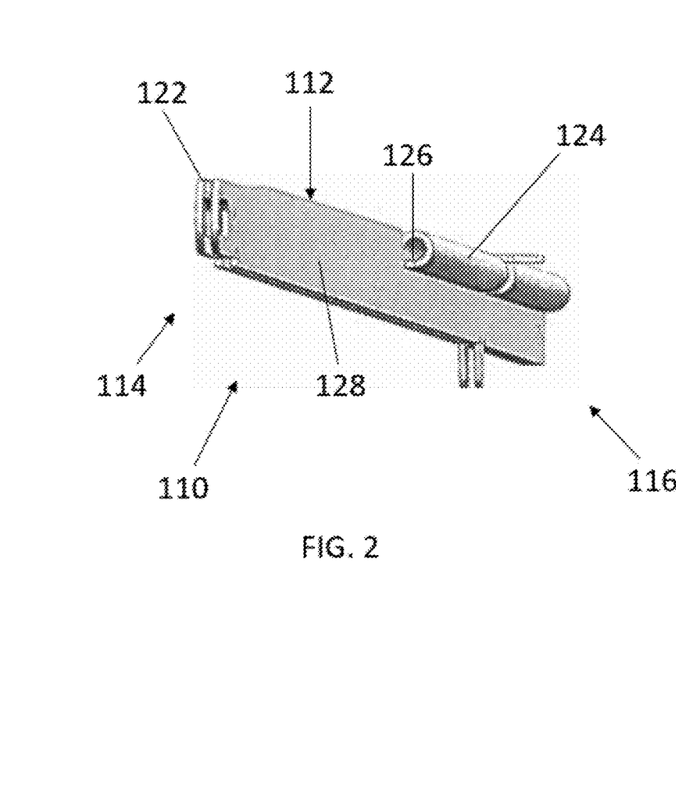
FIG. 2 is a perspective view from below and one side of a portion of a first embodiment of a drive shaft in accordance with a first aspect of the present invention.
Figure 3:
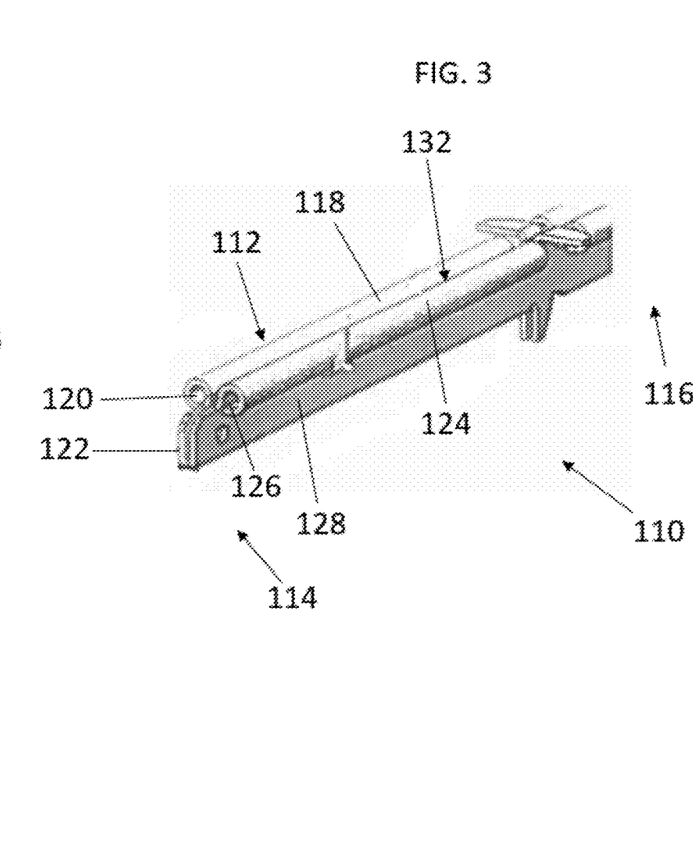
FIG. 3 is a perspective view from above and one side of the portion of the embodiment of FIG. 2.

Drive shaft 110 comprises an elongate body 112 defining a first axis, X, as show in FIGS. 2 and 3. Elongate body 112 is further provided with a distal end 114 and a proximal end 116.

Elongate body 112 further comprises a first curved portion 118 defining a first open channel 120 extending along a portion of the length of the elongate body 112. First curved portion 118 further comprises a first planar portion 122 extending from the first curved portion 118 in a non-parallel direction to axis X. For example, the first planar portion 122 may extend from the first curved portion in a direction transverse to axis X.

Elongate body 112 further comprises a second curved portion 124 defining a second open channel 126 extending along a portion of the length of the elongate body 112. Second curved portion 124 further comprises a second planar portion 128 extending from the second curved portion 124 in a direction substantially transverse to axis X.

First planar portion 122 and second planar portion 128 are substantially parallel to one another along their length.

Elongate body is further provided with bridge portion 130 located between first planar portion 122 and second planar portion 128, bridge portion 130 securely engaging with both first and second planar portions 122, 128.

Figures 4, 5:
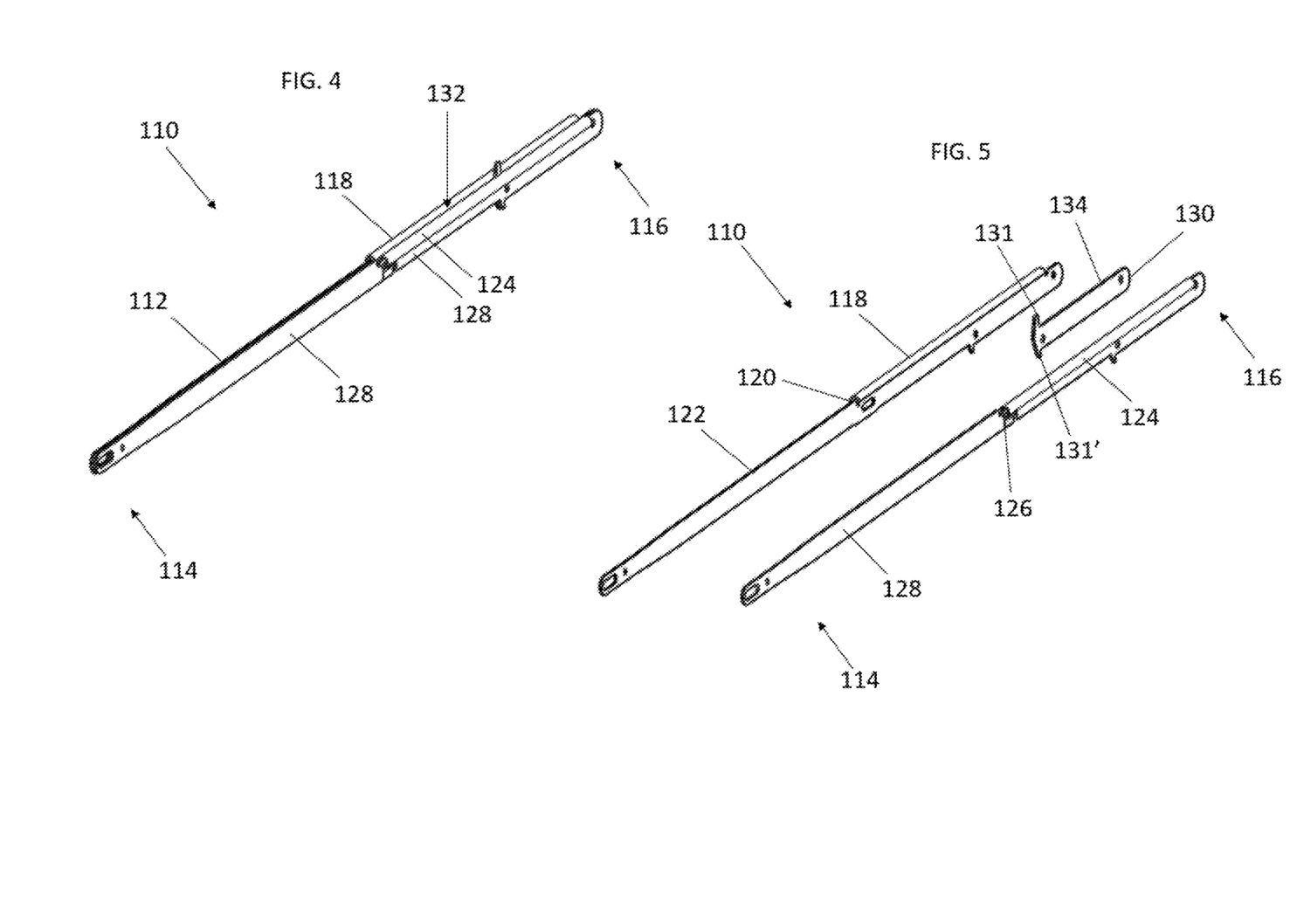
FIG. 4 is a perspective view from above and one side of the whole of the embodiment of FIG. 2.
FIG. 5 is an exploded view of the embodiment of FIG. 4.
Figure 6:
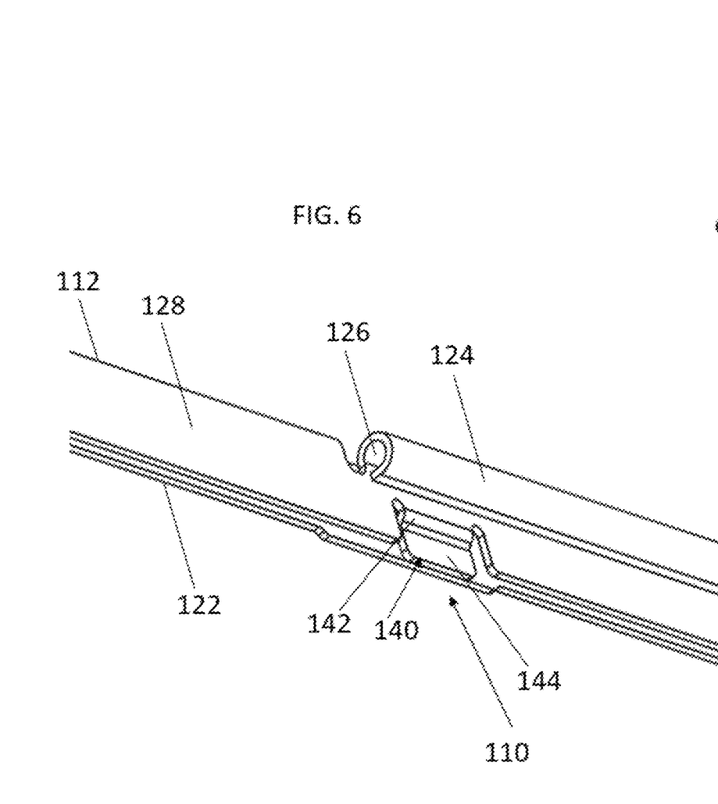
FIG. 6 is a partial view of a second embodiment of a drive shaft in accordance with a first aspect of the present invention.
Figure 7:
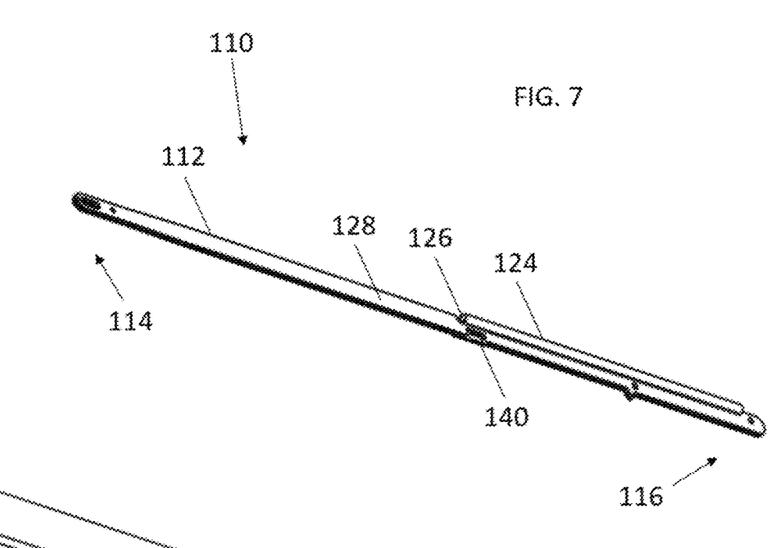
FIG. 7 is a complete view of the embodiment of FIG. 6.
Figures 8, 9:
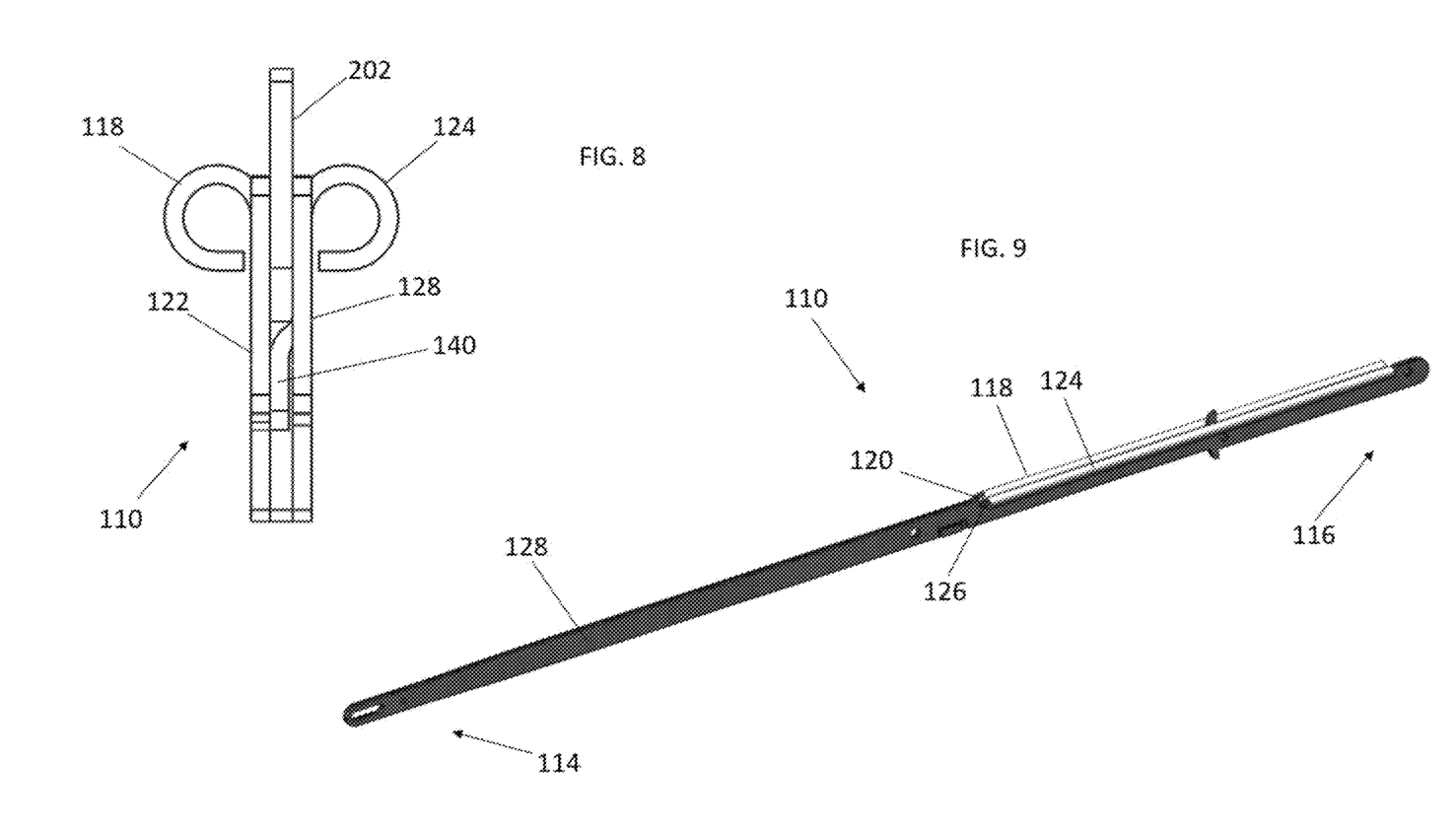
FIG. 8 is a view from one end of the embodiment of FIG. 6.
FIG. 9 is a perspective view from one side of a third embodiment of the present invention.

Bridge portion 130 is substantially planar, as can be seen in FIG. 5 and has first and second projections 131, 131', which are part of the mechanism that positions the handle of the surgical instrument relative to the cam pin and jaw cam slot of the surgical instrument within which the drive shaft 10 is located, in use.

Bridge portion 130 is welded to both the first and second planar portions 122, 128, thereby securing first and second planar portions 122, 128 to one another and holding them at a desired distance apart from one another so as to define a blade track 132 of desired width extending along the length of first and second planar portions 122, 128.

Thus, both the first and second planar portions 122, 128 are aligned with one another and extend parallel to axis X, and first planar portion 122 is spaced apart from the second planar portion 128 so as to define a recessed blade track 132 therebetween, the recessed blade track 132 extending parallel to axis X.

One end of the retractable blade will be supported by the cam pin or pivot pin of the jaws of the surgical instrument, and the other end will be supported by the body of the instrument that is held by the surgeon during use.

The limited length of the upper edge 134 of bridge portion 130 assist with positioning the blade during assembly.

Figures 10, 11:
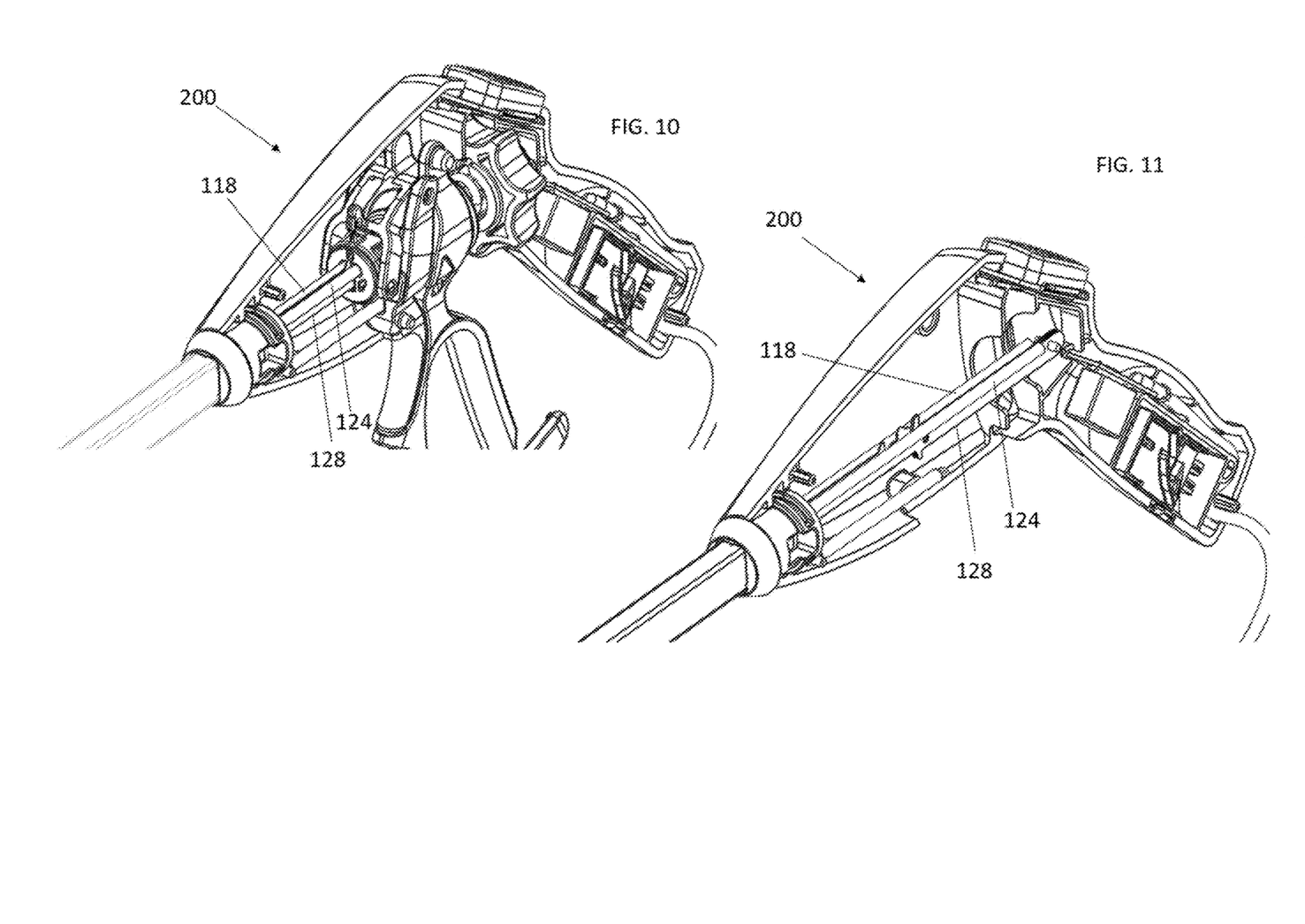
FIG. 10 is a cut-away of a perspective view of a surgical instrument handle including the embodiment of FIG. 6.
FIG. 11 is a cut-away of a perspective view of a surgical instrument handle of FIG. 10, with the drive and trigger mechanism parts removed.

First and second curved portions 118, 124 provide respective first and second open channels 120, 126 extending parallel to axis X, the tubular structures of each of the first and second open channels 120, 126 provide an integrated means of guiding and retaining wires extending through the mechanism of the handle of the surgical instrument during use. This is illustrated in FIG. 10 which shows the handle 200 of a surgical instrument incorporating a drive shaft 110 in accordance with the present invention, and also in FIG. 11 which shows the handle 200 of such a surgical instrument with the drive and trigger mechanism parts omitted to clearly show the location of drive shaft 110 within the instrument handle 200.

FIGS. 6 to 9 show a further embodiment of a drive shaft in accordance with the present invention in which second planar portion 128 is provided with a bridge portion comprising a cut-out portion 140 that is bent so as to form a first portion 142 extending at a non-parallel angle to the plane of first planar portion 122 and a second portion 144 extending parallel to the plane of first planar portion 122. The second portion 142 is welded to first planar portion 122 and acts as a spacer to retain first and second planar portions 122, 128 at a specific distance apart from one another so as to define a blade track 132 into which a retractable blade 202 extends during use of the draft shaft within a surgical instrument. As cut-out portion 140 of second planar portion 128 is integral to second planar portion 128 and acts as a spacer between the first and second planar portions 122, 128, it avoids the need for a separate bridge portion 130 to space the first and second planar portions 122, 128 apart from one another, thus simplifying the manufacturing process, without compromising on improved functionality.

The first portion 142 supports the mid-portion of a retractable base during use. Welded bridge portion 142 further serves to add stiffness to prevent the blade pinching between the first and second planar portions 122, 128 of the drive shaft during rotation of the drive shaft, when in use.

The width of blade track 132 is determined by the dimensions of first portion 142, with second portion 144 providing the surface for welded engagement with first planar portion 122.

Although in the embodiment shown in FIGS. 6 to 9, second portion 144 is welded to first planar portion 122, it is to be appreciated that alternative means of engagement known to the skilled person and suitable for secure engagement of the two parts may be used in addition to or as an alternative to welding. For example, the two parts could be adhered together using a suitable adhesive or in secure engagement with one another using physical fastening means and methods.

The invention claimed is:

1. A drive shaft for a bipolar surgical instrument, the drive shaft comprising:
   an elongate body (i) defining a longitudinal axis, (ii) having a proximal end portion and a distal end portion along the longitudinal axis, and (iii) comprising:
   a first portion defining a first open channel extending along a portion of a length of the elongate body; and
   a second portion (i) that is a separate component from the first portion and (ii) defining a second open channel extending along the portion of the length of the elongate body; and
   a spacer portion directly between the first and second portions in a direction of the longitudinal axis of the elongate body, wherein:
   longitudinal axes of the first and second portions and the longitudinal axis of the elongate body are parallel;
   the first portion and the second portion are configured such that the first portion is spaced from the second portion so as to define a recessed blade track between the first portion and the second portion;
   the recessed blade track extends parallel to the longitudinal axis of the elongate body; and
   side surfaces of the first and second portions are welded to the spacer portion.

2. The drive shaft as claimed in claim 1, wherein the first and second open channels comprise tube-like channels.

3. The drive shaft as claimed in claim 1, wherein the first and second open channels are adjacent the proximal end portion of the elongate body.

4. The drive shaft as claimed in claim 1, the elongate body further comprising a cam slot adjacent the distal end portion configured for engagement with first and second jaws of a surgical instrument.

5. The drive shaft as claimed in claim 1, wherein the spacer portion, the first portion and the second portion are configured such that a width of the spacer portion directly between the first and second portions determines a width of the recessed blade track.

6. A drive shaft for a bipolar surgical instrument, the drive shaft comprising:
   an elongate body (i) defining a longitudinal axis, (ii) having a proximal end portion and a distal end portion along the longitudinal axis, and (iii) comprising:
   a first portion defining a first open channel extending along a portion of a length of the elongate body; and a second portion (i) that is a separate component from the first portion and (ii) defining a second open channel extending along the portion of the length of the elongate body, wherein:
longitudinal axes of the first and second portions and the longitudinal axis of the elongate body are parallel;
the first portion and the second portion are configured such that the first portion is spaced from the second portion so as to define a recessed blade track between the first portion and the second portion;
the recessed blade track extends parallel to the longitudinal axis of the elongate body; and
each of the first and second portions defines a blade engagement surface configured to engage a blade of a surgical instrument.

7. A bipolar surgical instrument comprising:
a body;
an elongate shaft (i) attached to the body and (ii) extending to a distal end;
first and second opposed jaws at the distal end of the elongate shaft, the first jaw being movable with respect to the second jaw between an open position in which the first and second jaws are spaced apart from one another and a closed position in which the first and second jaws are adjacent one another, the first and second jaws having inner surfaces;
a drive shaft as claimed in claim 1, the drive shaft connected with at least the first jaw, the drive shaft being movable with respect to the body and the elongate shaft between a first position in which the jaws are in the open position and a second position in which the jaws are in the closed position; and
a blade that extends through the recessed blade track in the drive shaft to the first and second jaws,
an actuation grip (i) movably mounted on the body, (ii) configured to operate the drive shaft, and (iii) having a released position in which the drive shaft is in the first position and an engaged position in which the drive shaftrecessed blade track in the drive shaft is in the second position; and
wherein the first and second opposed jaws define a blade track which extends from a proximal end to a distal end of the first and second opposed jaws.

8. The bipolar surgical instrument as claimed in claim 7, further comprising a blade actuator configured to move the blade in the recessed blade track between a retracted position and a deployed position.

9. The bipolar surgical instrument as claimed in claim 8, wherein wires extend through the first and second open channels.

* * * * *